United States Patent [19]

Smidt

[11] Patent Number: 4,718,429
[45] Date of Patent: Jan. 12, 1988

[54] METHOD OF REDUCING FATTY DEPOSITS IN THE HUMAN BODY

[76] Inventor: Udo Smidt, 133, Filderstrasse, D-4130 Moers 1, Fed. Rep. of Germany

[21] Appl. No.: 588,116

[22] Filed: Mar. 9, 1984

[30] Foreign Application Priority Data

Mar. 10, 1983 [DE] Fed. Rep. of Germany ....... 3308553

[51] Int. Cl.⁴ ................................................. A61F 7/00
[52] U.S. Cl. .................................... 128/400; 62/259.3
[58] Field of Search ............... 128/400, 402; 62/259.3, 62/261

[56] References Cited

U.S. PATENT DOCUMENTS

| | | | |
|---|---|---|---|
| 2,110,022 | 3/1938 | Kliesrath | 128/400 X |
| 2,726,658 | 12/1955 | Chessey | 128/400 |
| 3,007,473 | 11/1961 | Jackson et al. | 128/400 |
| 3,074,410 | 1/1963 | Foster | 128/400 |
| 3,967,627 | 7/1976 | Brown | 128/400 |
| 4,118,946 | 10/1978 | Tubin | 128/400 X |

OTHER PUBLICATIONS

Therapeutic Heat & Cold, ed. by Justus F. Lehmann, 3rd. Ed., copyright 1982, pp. 187–189, 197, 198.

*Primary Examiner*—Anton O. Oechsle
*Attorney, Agent, or Firm*—Spensley Horn Jubas & Lubitz

[57] ABSTRACT

A device and related method for reducing fatty deposits in the human body. The device comprises a cooling panel adapted to be placed on a portion of the human body. The panel has at least one fluid conducting passage through which a coolant is flowed. In this manner, a part of the body is cooled thereby causing the body to consume fatty deposits to make up for heat loss.

8 Claims, 4 Drawing Figures

U.S. Patent   Jan. 12, 1988   4,718,429
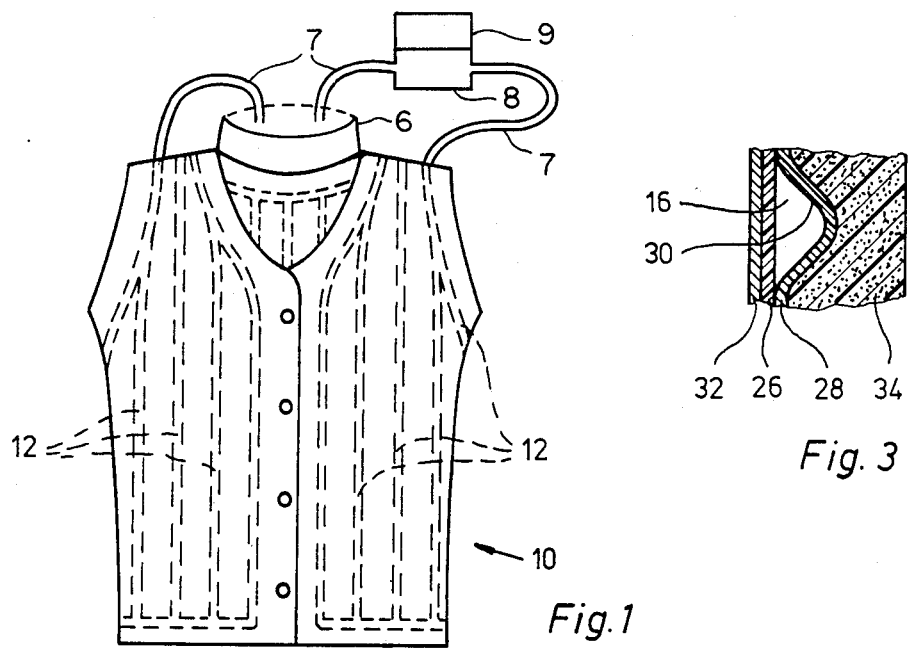
Fig. 1
Fig. 3
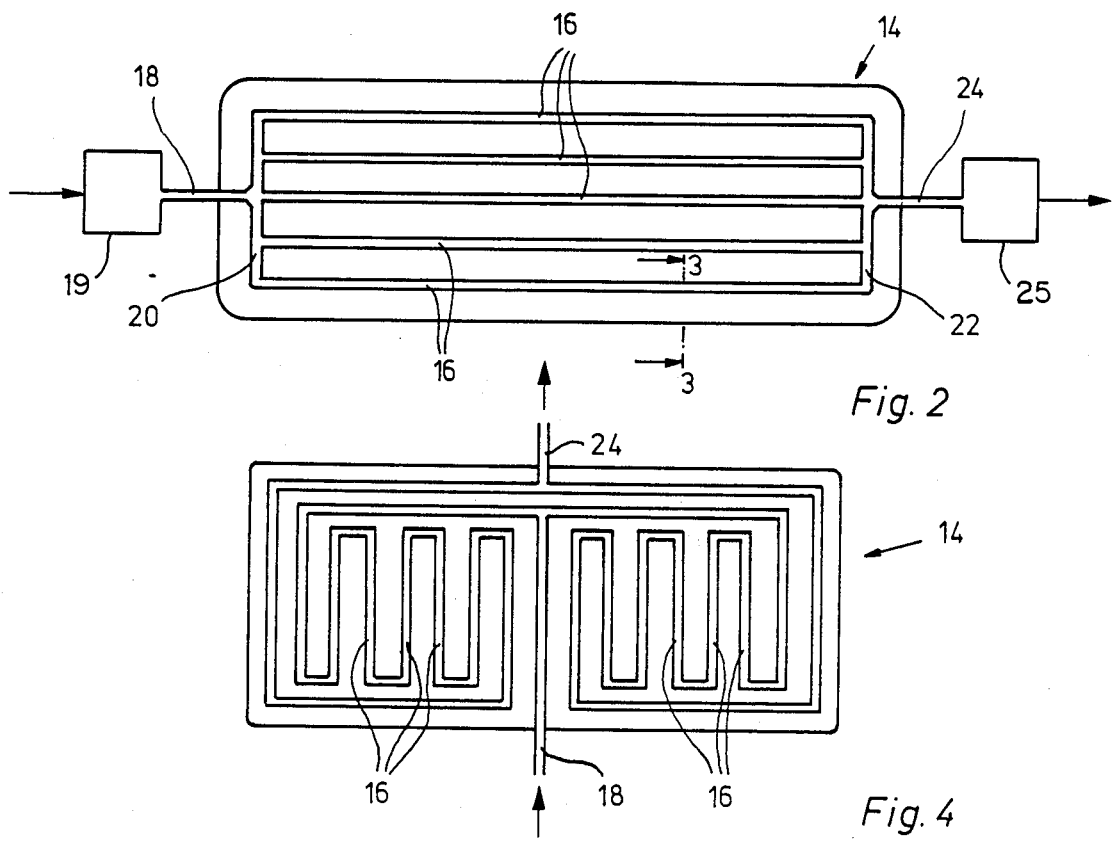
Fig. 2
Fig. 4

METHOD OF REDUCING FATTY DEPOSITS IN THE HUMAN BODY

BACKGROUND OF THE INVENTION

1. Field of the Invention

The present invention relates to a method of and a device for reducing fatty deposits in various parts of a human body by the extraction of heat, and more generally to a method of weight reduction.

2. Prior Art

It is well known in medicine that corpulence, overweight, and obesity are in an overwhelming number of cases not due to pathological causes, but rather to a positive energy balance. The efficiency of chemical processes in the bodies of obese persons such as the sodium/potassium pump is high whereby such persons produce and emit less heat and hence consume less energy than other persons. It is also well known in medicine that a human body produces heat by two routes, namely, (1) the reduced efficiency of certain chemical processes thereby producing more waste heat, and (2) muscular twitching, the energy-supplying chemical reactions required therefor also producing heat.

Common methods of human weight reduction include long-term diets to reduce the intake of food causing the deposition of fat in the human body and increased physical effort for the body to consume more energy. It is usual for such methods only to achieve a temporary reduction in weight, and not a permanent reduction because the efficiency of metabolic processes has not been changed.

SUMMARY OF THE INVENTION

It is the main object of the present invention to provide a method of reducing human weight by removing or reducing fatty deposits in a human body without the employment of surgery.

It is also an object of this invention to provide a method of causing a human body to draw on energy absorbed and mainly stored as fat to produce more heat, the method consisting of extracting of heat from the body.

To reduce or to remove fatty deposits from a human body, the present invention provides for a personal cooling device having a cooling fluid source and a cooling fluid panel to be placed on parts of the human body entering into a heat-exchange relationship therewith and thereby extracting heat from said parts. The aforementioned panel comprises one or several heat-exchange surface(s), one or several fluid conducting passage(s) running largely through the entire heat-exchange surface or surfaces, and one or several inlet(s) and one or several outlet(s) connected by said fluid conducting passage(s). The aforementioned device is further equipped with a conduit or several conduits taking relatively low temperature cooling fluid from the aforementioned cooling fluid source to said fluid conducting passage inlet or inlets and a conduit or conduits returning cooling fluid heated by the extraction of heat from a human body being treated and leaving the aforementioned fluid conducting passage or passages through the outlet or outlets thereof. The temperature of the aforementioned cooling fluid passing through the aforementioned cooling fluid panel is reduced below the surface temperature of the skin of the person being treated and the heat-exchange surface or surfaces of said cooling fluid panel is placed on the part or parts of the human body to be treated thereby entering into a heat-exchange relationship therewith. The cooling fluid has a controlled temperature and flows through the cooling fluid panel the heat-exchange surface or surfaces of the panel extracting heat from the adjacent surface part or parts of the human body being treated thereby reducing the temperature of said part or parts to 15° to 25° C., and preferably 19° to 22° C. It has been found that a reduction in a temperature of the surface part or parts of the human body being treated to a level such as 19° to 20° C. at night while the person being treated is asleep will not cause any deterioration in the constitution of the person, or cause the person to feel uncomfortable, but will effectively reduce or remove fatty deposits in the body of the person. The method which is the subject of this invention provides for the aforementioned cooling fluid panel to be placed on the surface part of the human body to be treated for a long period such as a few hours while the person being treated is asleep. Cooling fluid is then passed continuously through the cooling fluid panel thereby forcing the body of said person to consume fat deposited in the body being treated to compensate for the heat so lost seek to increase the temperature of said part of the body beyond its usual temperature.

In one embodiment of the present invention, the aforementioned cooling fluid panel may be a garment covering the parts of the body to be cooled and treated and to be worn by the person to be treated for the duration of the treatment. In another embodiment, the panel may be a blanket used in the place of a typical blanket at night.

If a uniform extraction of heat over a large part of the body of the person being treated is desired, the heat-exchange surface or surfaces of the aforementioned cooling fluid panel should preferably be coated by a thin metal foil such as aluminum foil.

The conduits to and from the fluid conducting passage or passages of the aforementioned cooling fluid panel may be integrated in a closed cooling cycle incorporating a cooling device to reduce the cooling fluid temperature. The cooling device may incorporate a cold storage system cooled by a separate cooling means and designed for extracting heat from the aforementioned cooling fluid. In one embodiment, the cold storage system may consist of a cold pack cooled before use.

In another embodiment, the aforementioned cooling device may incorporate a heat exchanger in heat-exchange relationship with a separate cooling means extracting from the aforementioned cooling fluid heat absorbed from the part or parts of the human body being treated. In a simple embodiment, the heat exchanger may be arranged or located in a tank or other vessel through which water from a cold water system is passed, the flow of water to and from said tank or vessel being controlled as a function of the water temperature. A pump driven by a motor or any other means may be used for circulating the aforementioned cooling fluid through the aforementioned cooling fluid device.

In another embodiment, the aforementioned cooling fluid panel may be an evaporator in a closed refrigeration cycle working according to the compression-type or the absorption-type refrigeration method.

A temperature measuring and/or indicating means may be incorporated in the conduits to and/or the conduit from the aforementioned cooling fluid panel. This enables one to compute and/or to control the heat extracted or being extracted from the body being treated from the cooling fluid panel inlet and/or outlet temperature or temperatures, the cooling fluid flow, the specific heat of the cooling fluid and the operating time of and the throughput through the pump circulating said cooling fluid.

To prevent excessive cooling of the part or parts of the human body being treated, a sensor or sensors of an adjustable thermostat controlling the flow of the aforementioned cooling fluid may be incorporated in the conduit to and/or the conduit from the aforementioned cooling fluid panel.

The aforementioned cooling fluid panel may, in addition to the aforementioned fluid conducting passage or passages, be fitted with a separate system of fluid conducting passages including upstream and downstream connecting conduits to carry a second fluid at a temperature different from the cooling fluid's temperature and more particularly a temperature above the cooling fluid temperature in order to rapidly reheat to the usual body temperature parts of the human body cooled by the method which is the subject of this invention. Alternatively such separate system may be used in order to exclude part or parts of the human body from treatment by the method which is the subject of this invention, said second system of fluid conducting passages being adopted to exclude kidneys which are particularly sensitive to low temperature or other parts of the body from such treatment if the entire trunk or another large part of the body is covered by a device such as a cooling jacket which is the subject of this invention.

BRIEF DESCRIPTION OF THE DRAWINGS

The present invention is now described in a nonlimitative way with reference to the accompanying drawings.

FIG. 1 is a schematic front view of a cooling fluid panel in accordance with the present invention embodied as a vest to be worn by the person to be treated.

FIG. 2 presents a schematic top view of a cooling fluid panel designed in accordance with the present invention and embodied as a blanket with parallel fluid conducting passages.

FIG. 3 is a cross-sectional view taken on the line 3—3 of FIG. 2.

FIG. 4 is a top view of a cooling fluid panel embodied as a blanket as in FIG. 2 with the arrangement of the fluid conducting passages having been modified.

DETAILED DESCRIPTION OF THE DRAWINGS

FIG. 1 is a schematic of a cooling fluid panel embodied as a vest 10 worn by a person for treatment by the method which is the subject of the present invention. The vest being made of two layers of thermoplastic sheeting impermeable to liquids and gases. The fluid conducting passages 12 indicated in FIG. 1 by broken lines may be obtained by welding the two plastic sheets along the edges of the passages. A liquid, vapor or gas is directed into and out of the fluid conducting passages 12 through one or several upstream and downstream conduits (not shown in FIG. 1). The conduits are connected to the fluid conducting passages 12 so that said liquid, vapor or gas, acting as a cooling fluid, flows regularly through all such passages. The conduit or conduits to and from the fluid conducting passages may be connected with the passages at a variety of points, such as the bottom back edge of the vest, and the back part of the neck of the vest. The aforementioned cooling fluid enters the conduit or conduits, flows through the fluid conducting passages and exits through the conduit or conduits from the fluid conducting passages. The cooling fluid is then preferably directed through a cooling fluid tank 6 or another cooling fluid container strapped on the back of the person being treated or located at any other point. Hoses 7 are used to connect the tank or container with the conduits to and from the fluid conducting passages. The method of cooling fluid circulation may, if a liquid is used, be by gravity feed. Water under pressure (e.g., tap water) or a circulation pump 8 driven by a motor may also be used, for improved cooling fluid flow control, as a function of the heat to be extracted from the body of the person being treated by means of the cooling fluid panel. In this embodiment, the start-up and shut-down of said pump is controlled by controller 9 as a function of the temperatures of the cooling fluid entering and leaving the fluid conducting passages. If the method which is the subject of the present invention is embodied by a conventional compression or absorption type refrigeration system, cooling fluid flow will be of the forced circulation type and may be controlled by a thermostat. If heat extraction from the body of the person being treated is not to be limited to the upper part of the trunk, and heat is to be extracted from other parts of the body such as the arms, the aforementioned cooling fluid panel will not be embodied by the vest described. Rather, a jacket-type or overalltype structure is used fitted with fluid conducting passages in hose parts which cover portions of the body from which heat is to be so extracted. Those portions of the body which are sensitive to low temperature are protected by omitting fluid conducting passages from the parts of the structure covering such sensitive portions of the body.

FIG. 2 is a schematic of a rectangular blanket-type embodiment 14 of the cooling fluid panel fitted with parallel fluid conducting passages 16 receiving the cooling fluid through an upstream conduit 18 and a header 20. FIG. 2 also illustrates a means 19, such as a temperature controller, for regulating/controlling the temperature of the cooling fluid as it flows into the panel. The cooling fluid leaving the fluid conducting passages flows through a downstream header 22 and a downstream conduit 24. In some embodiments, a conventional heat exchanger (e.g., a refrigerator) 25 may be used to decrease the temperature of the fluid to 13°-23° C. before the fluid is directed back to the panel. The depicted blanket-type embodiment 14 of the aforementioned cooling fluid panel may be used in any one of a variety of different forms such as by placing it on a mattress and/or incorporating it in a bed cover. This provides the added advantage that heat may be extracted from the body of the person being treated while said person is at rest without restricting said person by a tightfitting structure.

FIG. 3 provides a cross-sectional view of the blanket 14 depicting the layered structure of said blanket 14 as consisting of two flexible thermoplastic sheets 26, 28 FIG. 3 also illustrates that any of the fluid conducting passages 16 may be obtained by pressing or otherwise forming channel-type cavities 30 in the thermoplastic sheeting 28 located distant from the body being treated. The cavities in the thermoplastic sheeting 28 and the flat thermoplastic sheeting 26 which is closer to the body being treated and welded to sheeting 28 along the edges of said cavities form the closed fluid conducting passages 16. Aluminum foil 32 is used to coat sheeting 26 to improve the absorption of heat from the adjacent parts of the body of the person being treated.

The external side of sheeting 28 is coated which a thick thermally insulating layer 34 of expanded plastic material such as polyurethane foam. Layer 34 is used for thermal insulation of the fluid conducting passages 16 and prevents heat absorption from the environment. It also provides protection for the fluid conducting passages 16 against compressive loads.

If the aforementioned cooling fluid panel is embodied as a garment such as the vest depicted in FIG. 1, the aforementioned thermally-insulating layer may also take the form of an insulating garment separate from the garment 10.

FIG. 4 also depicts a blanket-type embodiment 14 of the aforementioned cooling fluid panel largely designed like the blanket-type embodiment of the cooling fluid panel described hereinabove with reference to FIGS. 2 and 3. However, in the case depicted in FIG. 4, the fluid conducting passages 16 are not straight fluid conducting passages arranged parallel and running from one short side of said panel to the other short side of said panel as described hereinabove. Rather, they are now arranged in a looped pattern which is symmetrical about the centerline of said blanket-type panel 14, the upstream line 18 and the downstream line 24 being connected to the fluid conducting passages approximately in the center of the opposite long sides of the blanket-type panel 14. It is obvious that such an arrangement of the fluid conducting passages in the cooling fluid panel will produce a temperature distribution on the surface of said panel which will differ from the temperature distribution obtained by an arrangement of the type depicted in FIG. 2.

It is apparent that a large variety of modifications of the present invention are feasible. These modifications may, for example, relate to the arrangement and the location of the heat extracting parts of the aforementioned cooling fluid panel, and the pattern of fluid conducting passages (which may, for instance, be a meander-type or a circular arrangement). The distribution of the passages in the cooling fluid panel may be uniform or irregular for a variety of reasons such as increased heat extraction through certain parts and less heat extraction through certain other parts of the heat exchange surface or surfaces of said cooling fluid panel. If desired, parts of said cooling fluid panel may be without fluid conducting passages thereby preventing heat extraction at such points. Separate systems of fluid conducting passages connected to separate upstream and downstream conduits may be provided to flow fluids of different temperatures such as a cooling fluid and a heated fluid so that part of the panel will extract heat from the body of the person being treated and part of the panel will supply heat to the body of the person being treated. In another aspect of the invention, heat extraction is not only controlled locally with respect to the part of the body from which heat is extracted, but also as a function of time varying the temperature of the cooling fluid in a variety of modes such as an increase in the temperature following treatment in order to remove any unpleasant feeling of subcooling to the part of the person being treated.

The cooling fluid used for the the purposes of the present invention may be a variety of liquids such as water or a solution such as saline solution which is cooled by an appropriate means when it returns from the aforementioned cooling fluid panel. If desired, any of the fluorocarbon refrigerants frequently used in refrigeration systems which are liquid or gaseous depending on pressure and temperature conditions may be used for flowing through the aforementioned cooling fluid panel which will then perform the functions of an evaporator in a refrigeration system.

This invention, therefore is not limited to the specific illustrations set forth and discussed above.

What I claim is:

1. A method of reducing or removing fatty deposits in a human body comprising the steps of:
   (a) providing a cooling device having a cooling fluid source and a cooling fluid panel adapted to be placed on the human body having the fatty deposits for reducing the skin surface temperature by entering into a heat-exchange relationship therewith, said panel comprising at least one heat-exchange surface, at least one fluid conducting passage running largely through said heat-exchange surface, a inlet conduit for directing relatively low-temperature cooling fluid from said cooling fluid source into said fluid conducting passage, an outlet conduit for directing relatively high-temperature cooling fluid out of said fluid conducting passage, and means for controlling the temperature of the cooling fluid flowing as it flows into said cooling fluid panel;
   (b) placing said heat-exchange surface of said cooling fluid panel on a surface portion of a human body in a heat exchange relationship therewith;
   (c) flowing a cooling fluid through said cooling fluid panel;
   (d) providing a temperature controlling means for controlling the temperature of said fluid such that heat is extracted by said heat exchange surface from the surface portion of said human body adjacent to said heat exchange surface thereby reducing the temperature of said surface portion to a temperature between about 15° and 25° C.; and
   (e) maintaining said cooling fluid panel on said surface portion of said human body to be treated for a period of time sufficient for said human body to consume fatty deposits to make up for heat loss to the cooling device.

2. A method according to claim 1 whereby said heat exchange surface extracts heat from the surface of the human body being treated sufficient to reduce the temperature of said body surface portion to about 19° to 22° C.

3. A method according to claim 1 wherein said cooling device further includes a heat exchanger joined to said outlet conduit, and said method includes the step of flowing said cooling fluid through said heat exchanger such that said temperature of the fluid is reduced to about 13° to 23° C.

4. A method according to claim 1 wherein said cooling fluid panel is an evaporator in a closed cooling cycle of a refrigeration system.

5. A method according to claim 1 further including a temperature measuring means joined to said cooling device.

6. A method according to claim 5 wherein said temperature measuring means further includes an adjustable thermostat for controlling the rate of flow of said cooling fluid.

7. A method according to claim 1 further including the step of providing a fluid flow controlling means for controlling the cooling fluid flow rate as a function of the difference between the temperatures of said cooling fluid upstream and downstream of said fluid conducting passage.

8. A method according to claim 5 wherein said temperature measuring means further includes an adjustable thermostat for controlling the temperature of said cooling fluid.

* * * * *